United States Patent [19]

Frazer

[11] Patent Number: Plant 6,872

[45] Date of Patent: Jun. 20, 1989

[54] DIEFFENBACHIA HYBRIDA BALI HAI

[75] Inventor: Edwin J. Frazer, Brisbane, Australia

[73] Assignee: Hartman Plant Laboratories, Inc., Santa Paula, Calif.

[21] Appl. No.: 23,609

[22] Filed: Mar. 9, 1987

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Hale and Dorr

[57] ABSTRACT

A new and distinct cultivar of Dieffenbachia known as Dieffenbachia Hybrida Bali Hai which is a seedling cross between Dieffenbachia Rex and an unnamed Rex hybrid.

1 Drawing Sheet

The invention comprises a new and distinct cultivar of Dieffenbachia known as Dieffenbachia Hybrida Bali Hai.

The new cultivar is a product of a seedling cross between Dieffenbachia Rex and an unnamed Rex hybrid.

The following observations, measurements and values describe plants grown in Alva, Fla. under greenhouse conditions that closely approximate those generally used in horticultural practice. All color references are measured against The Royal Horticultural Society Colour Chart. Colors are approximate as color depends on horticultural practices such as light level and fertilization rate among others.

The following traits have been repeatedly observed to be characteristics which in combination distinguish Dieffenbachia Bali Hai from other commercially available Dieffenbachia.

Distinctions

1. New leaves have spots that are chartreuse fading to white with age.
2. The leaves are large and black-green with clearly defined white blotches, and the pattern is variable from leaf to leaf.
3. The midrib is flexible enough to enable touching the tip of the leaf to its base without damage.
4. The stem and petioles are highly colored with white and white and green stripes.
5. The petioles clasp the stem tightly with fleshy wings.
6. The new leaves are positioned close to vertical giving the plant height yet becoming more horizontal with age giving the plant width.
7. The breaks are numerous for its size and quickly develop large leaves which color early.
8. The combination of clasping petioles, large leaves which become horizontal with age and numerous large leaved breaks create a plant habit of bushiness that is uncommon for a Dieffenbachia of this height and age.
9. Bali Hai finishes in a 6" pot faster than other Dieffenbachia of its size.
10. Leaves are flexible, so shipping causes less damage.

The appearance and distinctive character of Bali Hai is shown in the FIGURE which is a true color photograph of the cultivar in an eight-inch pot.

DESCRIPTION

Propagation: Asexual production either through tissue culture or division.

Plant: In a 6 inch pot, Bali Hai will be approximately 20 cm to 24 cm from the soil surface to the junction of the petioles of the last two unrolled leaves and approximately 40 cm to 48 cm in width after approximately 26 weeks to 36 weeks under appropriate growing conditions from tissue culture. All measurements are based on the above parameters.

Stem:

*Growth pattern.*—The stem is upright in growth and will be approximately 2.7 cm to 3.3 cm in diameter at a height of 5 cm above the soil surface. Internode distance will be approximately 1.5 cm to 2.2 cm at a height of 3 cm above the soil.

*Color.*—The stem is striped with coarse lines of dark green and light greenish white similar to the leaf color.

Petiole (based on the fourth expanded leaf from apex of the dominant shoot):

*Pattern.*—The petiole has fleshy edges extending from the midrib that will be referred to as wings. The wings will be approximately 11 mm to 15 mm wide 1 cm below the leaf base. The wings extend from the base of the petiole to within approximately 1.5 cm to 2.0 cm of the leaf base. The apex of the wings is emarginate. The petiole follows the stem axis but diverges from the axis approximately 2.0 cm to 3.0 cm from the leaf base forming a horizontal distance from the edge of the stem to the leaf base of approximately 0.7 cm to 1.3 cm.

*Physical dimensions.*—The petiole will be approximately 10 cm to 14 cm from its base to the base of the leaf. The petiole will be approximately 8 mm to 12 mm in diameter one-half way between the top of the wing to the bottom of the leaf.

*Color and color pattern.*—The petiole and wings will have wide stripes and blotches of white, dark green and light green running parallel to the central axis and the midrib will be the same.

Leaf:

*Growth pattern.*—The leaf will be oval with a cuspidate apice and a cordate/sagittate base. The margin is entire. The leaf is asymmetric with the side of the leaf unrolling first having less surface area and less undulations on the leaf margin than the side unrolling last. The leaf is oriented parallel to the stem axis at the time of full unrolling changing to horizontal to the stem axis as more leaves unroll above it. The midrib does not droop over the length of the leaf. The leaf blade is flat from the midrib to the margin.

*Physical dimensions.*—For the potsize and growing time indicated, the largest leaf will be approximately 34 cm to 40 cm long and approximately 18 to 21 cm wide. An average sized leaf will be approximately 24 cm to 28 cm long and approximately 13 cm to 16 cm wide. The leaf thickness is medium.

*Midrib.*—The midrib is thick and has the same color combination as the petioles.

*Primary veins.*—The primary veins are sunken into the adaxial side and protruding out of the abaxial side.

*Color and pattern.*—The adaxial surface of both the mature, older leaf and the newly-opened leaf has a midrib color of 157C, blotched with 135A, and a leaf blade background color blacker than 135A, blotched with areas of 157C and small dots of 1C. The abaxial surface of the mature, older leaf and the newly-opened leaf has a midrib color of 146D and a leaf blade background color of 137D with blotches of 146D and 157B.

Axillary breaks: There will be approximately 6 to 9 axillary breaks with at least 1 leaf expanded. Leaves will show color by the second leaf and will have true color and pattern by the fourth leaf.

Inflorescences: Not present.

Roots: Thick white roots with finer laterals.

General observations: Dieffenbachia Bali Hai is truly distinctive in color, pattern and form. It finishes quickly in a 6" pot. The combination of leaves, clasping petioles and breaks give a tall, wide and dense appearance unusual for a plant that grows this quickly, The new leaves open up with chartreuse spots that turn to white with age.

I claim:

1. A new and distinct cultivar of Dieffenbachia as described and illustrated.

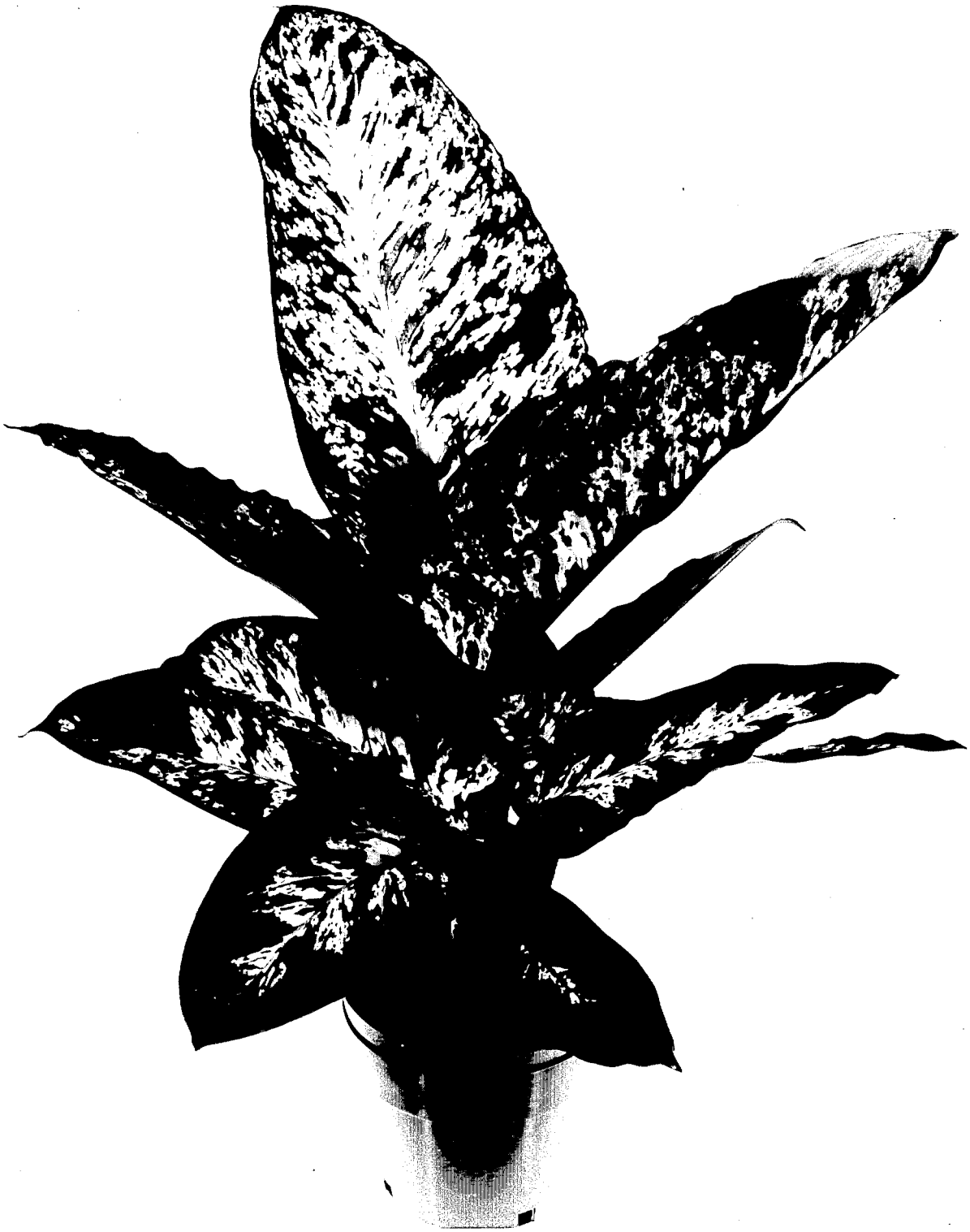

* * * * *